United States Patent [19]

Igaki et al.

[11] Patent Number: 5,109,428
[45] Date of Patent: Apr. 28, 1992

[54] MINUTIA DATA EXTRACTION IN FINGERPRINT IDENTIFICATION

[76] Inventors: Seigo Igaki, Hiraojutaku 59-103, 474, Hirao, Inagi-shi, Tokyo 206; Takashi Shinzaki, Fujitsu Atsugiryo 305, 2-3-10, Sakae-cho, Atsugi-shi, Kanagawa 243; Fumio Yamagishi, 5-541, 40-1, Oya, Ebina-shi, Kanagawa 243-04; Hiroyuki Ikeda, 7, Mugita-cho 1-chome, Naka-ku, Yokohama-shi, Kanagawa 231; Hironori Yahagi, 3-3-5-302, Tobio, Atsugi-shi, Kanagawa 243-02, all of Japan

[21] Appl. No.: 446,660

[22] Filed: Dec. 6, 1989

[30] Foreign Application Priority Data

Dec. 6, 1988 [JP] Japan ................................ 63-309067
Dec. 9, 1988 [JP] Japan ................................ 63-312533
Sep. 28, 1989 [JP] Japan ................................ 1-253458

[51] Int. Cl.⁵ .......................................... G06K 9/00
[52] U.S. Cl. ........................................ 382/5; 382/4; 356/71
[58] Field of Search ...................... 382/4, 5; 356/71

[56] References Cited

U.S. PATENT DOCUMENTS 4,752,966  6/1988  Schiller .................................. 382/5
4,933,976  6/1990  Fishbine et al. ........................ 382/4

FOREIGN PATENT DOCUMENTS 60-015779  1/1985  Japan.
60-084677  5/1985  Japan.
61-272886  12/1986  Japan.
63-000679  1/1988  Japan.

Primary Examiner—Leo H. Boudreau
Assistant Examiner—Barry Stellrecht

[57] ABSTRACT

An apparatus used in fingerprint identification for extracting minutia data from fingerprint image data. An optical sensor unit optically produces a sequence of fingerprint image data during a single operation of pressing a fingerpad onto an inspection plate in a direction substantially transverse to the plate and with increasing pressure over a time interval. A data storing unit stores the produced fingerprint image data in the form of a sequence of fingerprint image data obtained during the single operation of pressing the fingerpad onto the inspection plate. The stored fingerprint image data is utilizable for identification of the fingerprint.

4 Claims, 9 Drawing Sheets

| COORDINATE | | APPEARANCE FREQUENCY |
|---|---|---|
| $X_1$ | $Y_1$ | $W_1$ |
| $X_2$ | $Y_2$ | $W_2$ |
| $X_3$ | $Y_3$ | $W_3$ |
| ⋮ | ⋮ | ⋮ |
| $X_m$ | $Y_m$ | $W_m$ |

TIME-1

TIME-2

TIME-3

TIME-4

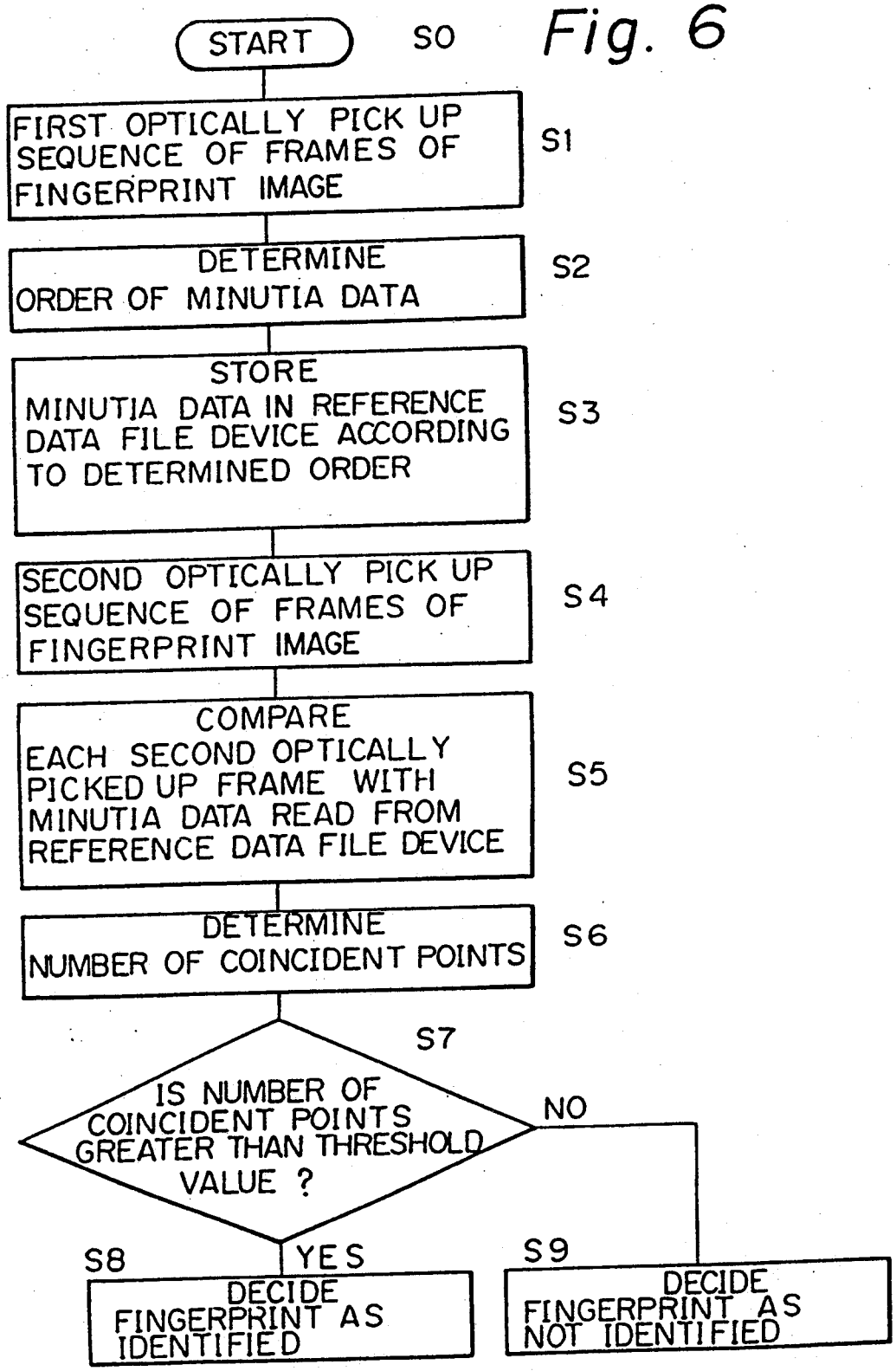

RIDGE PORTION OF FINGERPRINT PICTURE

REGION NUMBER (R1 TO R9)

RIDGE CENTER LINE

MINUTIA DATA EXTRACTION IN FINGERPRINT IDENTIFICATION

BACKGROUND OF THE INVENTION

1. Field of the Invention

The present invention relates to an apparatus and method used in fingerprint identification for extracting minutia data (characteristic point data) from a fingerprint image data.

2. Description of the Related Arts

In personal identification systems using fingerprint identification, a fingerprint identification method has been proposed to ensure the correctness of the registered fingerprint data in which minutiae (characteristic points) having a high frequency of appearance are adopted as the registered data. Usually, the minutia is an end point or a branch point of a ridge line of a fingerprint.

In this method, the optical picking-up of the fingerprint data using the same fingerpad (the palm side of a human fingertip) is carried out repeatedly, assigning the appearance frequency to each minutia, selecting a predetermined number of the minutiae from those having the highest appearance frequency to those having lower appearance frequencies, and adopting the thus selected minutiae as the data to be registered.

In this method, however, since a plurality of operations of picking-up of the fingerprint image using the same fingerpad are required, it is troublesome for the person whose fingerprint is being picked up to carry out such a plurality of picking-up operations, and further, it is necessary to carry out an alignment between minutiae because the location of the second operation of pressing down of the fingerprint after the lifting of the fingerprint after the first operation of pressing down of the fingerprint does not usually coincide with the location of the fingerprint in the first pressing down operation.

SUMMARY OF THE INVENTION

An object of the present invention is to provide an improved apparatus and method for use in fingerprint identification for extracting minutia data from fingerprint image data in which a plurality of picking-up operations of the fingerprint image data is carried out by performing only a single operation of pressing down of the fingerpad, on a sensor the alignment between successive fingerprint image data produced in successive, multiple fingerprint pressing down operations as in the prior art becomes unnecessary, and the troublesome process of the repeated fingerpad pressing down operations is eliminated.

In accordance with the present invention, there is provided an apparatus used in fingerprint identification for extracting minutia data from fingerprint image data and registering data for fingerprint identification based on the extracted minutia data, the apparatus comprising: optical sensor means for optically producing a sequence of fingerprint image data during a single operation of pressing a fingerpad in a single direction onto an inspection plate (i.e., the single direction being substantially transverse to the inspection plate and without any substantial sideways, or lateral, relative movement between the fingerpad and the inspection plate); and data storing means for storing the produced fingerprint image data in the form of a sequence of fingerprint image data obtained during the single operation of pressing the fingerpad in a single direction onto the inspection plate, the stored fingerprint image data being able to be utilized for fingerprint identification.

Also, there is provided a method, for use in fingerprint identification, for extracting minutia data from fingerprint image data and registering data for fingerprint identification based on the extracted minutia data, the method comprising the steps of:

optically obtaining a sequence of fingerprint image data during the single operation of pressing a fingerpad in a single direction onto an inspection plate; and storing the obtained fingerprint image data in a storage device in the form of a sequence of fingerprint image data obtained during the single operation of pressing the fingerpad in a single direction onto the inspection plate the stored fingerprint image data being utilize a fingerprint identification.

BRIEF DESCRIPTION OF THE DRAWINGS

FIG. 4 shows an example of the file form used in the apparatus of FIG. 3;

FIGS. 6 and 7 show flow charts of the process of operation of the apparatus for fingerprint identification according to other embodiments of the present invention;

DESCRIPTION OF THE PREFERRED EMBODIMENTS

Figure 1A:
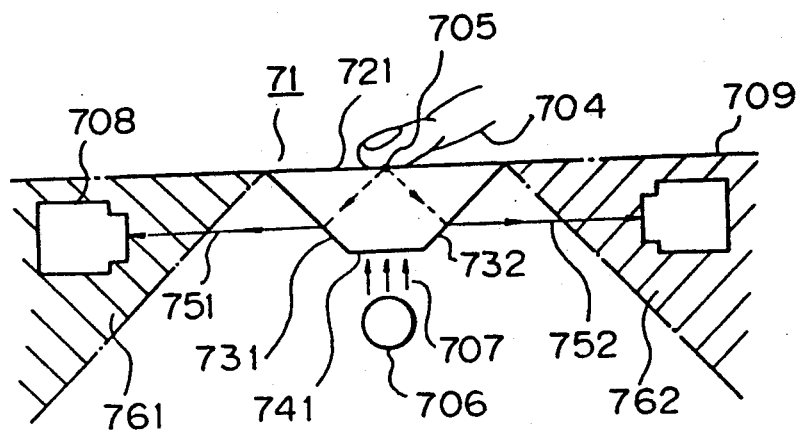
FIGS. 1A and 1B illustrate a prior art fingerprint identification method.

Before describing the preferred embodiments, prior art fingerprint identification methods are explained with reference to the illustrations of FIGS. 1A, 1B, 2A, and 2B. In a prior art apparatus shown in FIG. 1A, a fingerprint sensor 711 is constituted by a triangular prism of optical glass in which the vertex portion is cut. The fingerprint sensor 71 has an upper plane 721 against which a finger 704 is pressed, a lower plane 741 through which a light 707 from a light source 706 is irradiated perpendicularly and upwardly, and a pair of slant planes 731 and 732 through which the light is delivered. The photographic regions 761 and 762 are formed on the sides of the slant planes 731 and 732 through which the reflected light from the ridge 705 of the fingerprint passes but the reflected light from the groove of the fingerprint and the irradiation light 707 do not pass.

When the finger 704 is pressed onto the upper plane 721 and the light 707 is irradiated thereon through the lower plane 741, portions 751 and 752 of the reflected light from the ridge 705 of the fingerprint are delivered through the slant planes (i.e., slanted planar surfaces)

731 and 732, the light portions 751 and 752 delivered through the slant planes 731 and 732 are supplied to the pick-up elements 708 and 709, and accordingly, two pictures of the ridge 705 of the fingerprint are photographed simultaneously by the pick-up elements 708 and 709.

Figure 1B:
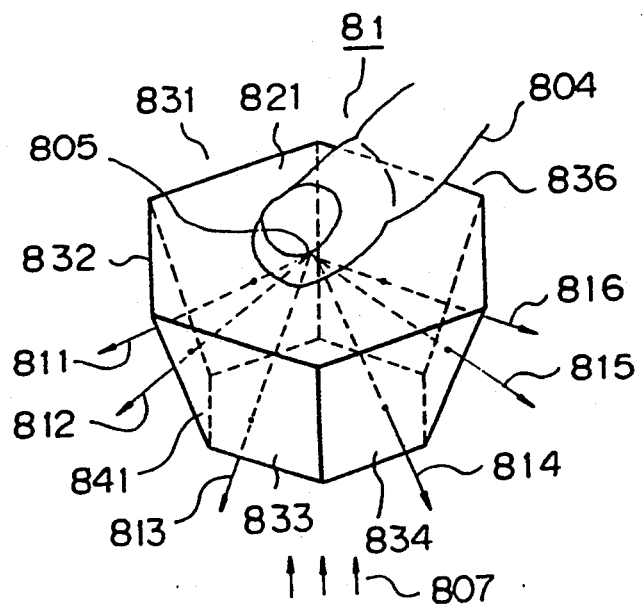
Figure 2A:
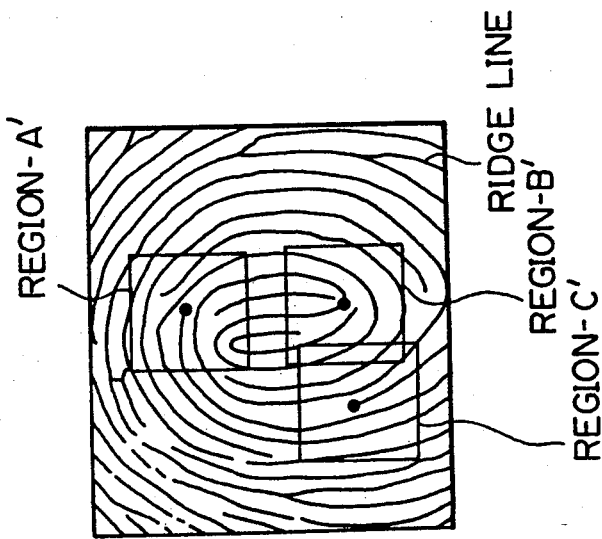
FIGS. 2A and 2B illustrate another prior art fingerprint identification method.
Figure 2B:
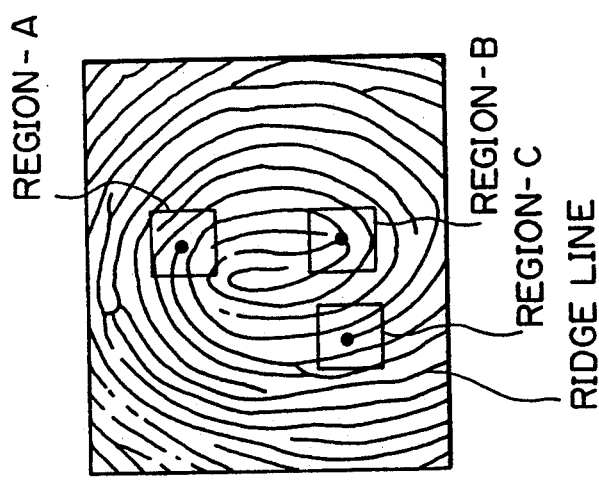

In another prior art apparatus shown in FIG. 1B, a fingerprint sensor 81 is constituted by a hexagonal pyramid of optical glass having an upper plane 821 onto which the finger 804 is pressed, a lower plane 841 through which the light 807 is irradiated, and six slant planes 831 to 836 through which the reflected lights 811 to 816 are delivered. The photographic regions (not shown) are formed similarly as in FIG. 1A.

When the finger 804 is pressed onto the upper plane 821 and the light 807 is irradiated through the lower plane 841, portions 811 to 816 of the reflected light from the ridge 805 of the fingerprint are delivered through the slant planes 831 to 836 and supplied to six pick-up elements (not shown), and accordingly, six pictures of the ridge 805 of the fingerprint are photographed simultaneously by the six pick-up elements.

Figure 3:
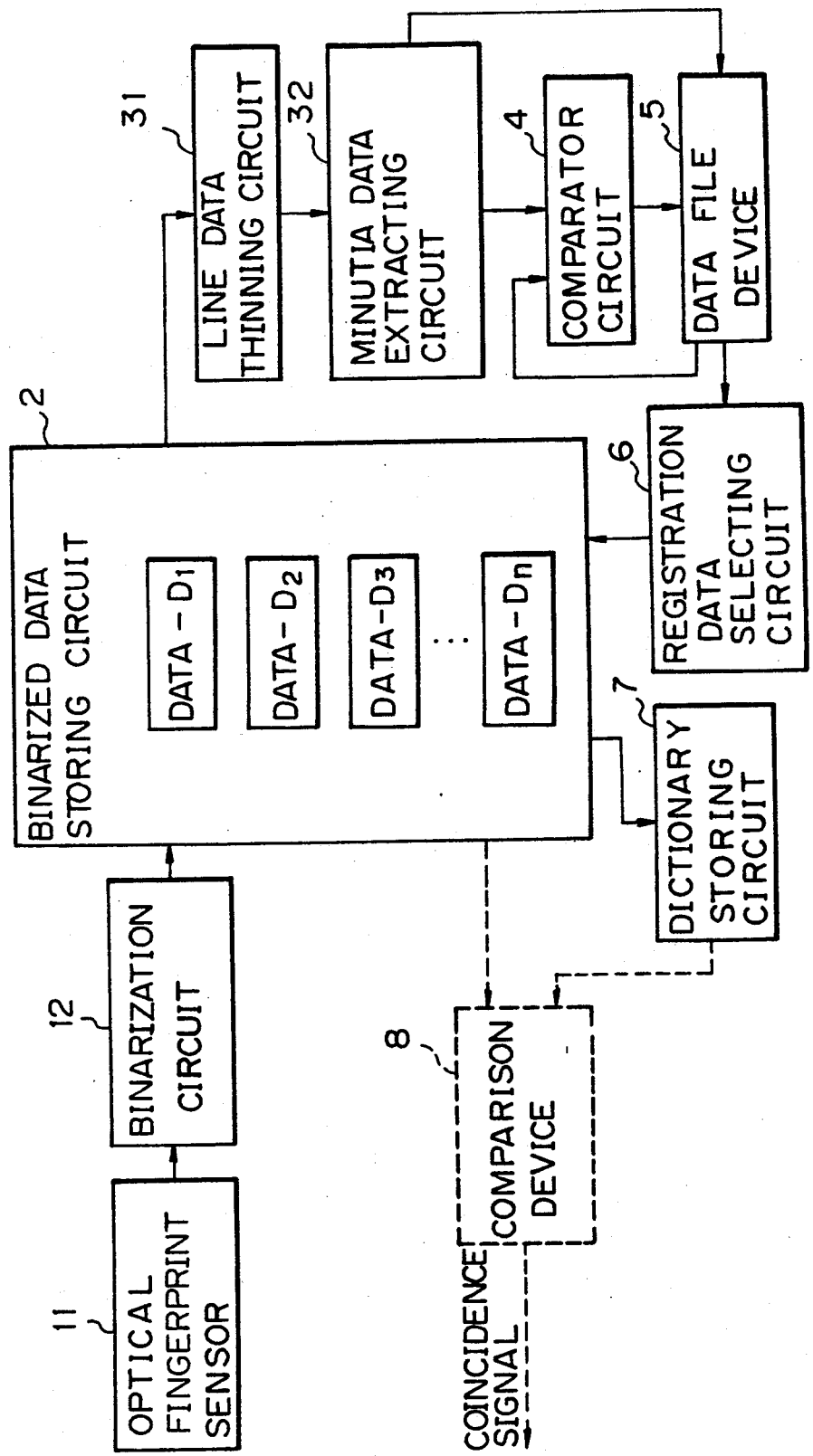
FIG. 3 is a schematic diagram of an apparatus for fingerprint identification according to an embodiment of the present invention.

An apparatus for fingerprint identification according to an embodiment of the present invention is shown in FIG. 3. The apparatus of FIG. 3 is constructed to provide sensor means for sensing a sequence of fingerprint pictures appearing during pressing of a fingerpad onto the inspection plate of a fingerprint sensor, and storage means for storing each fingerprint image of the sequence of fingerprint images sensed by the sensor means.

In the apparatus of FIG. 3, there are provided a fingerprint sensor 1, a circuit 2 for binarizing the fingerprint data, a binarized data storing circuit 3 having a sequence of frame memories, a line data thinning processing circuit 4, a minutia extraction circuit 5, a data file device 6, a comparator circuit 7, a registration data selection circuit 8, a dictionary storing circuit 9, and a comparison circuit 10.

The fingerprint sensor 1 is used for picking-up fingerprint images. The pick-up element of the fingerprint sensor is, for example, a charge-coupled device (CCD). In the CCD in which a large number of pixels are arranged in a plane, one fingerprint picture, i.e., one frame, is produced by scanning these pixels. For example, in the fingerprint sensor 1 of the CCD type, about 30 pixels are picked up per second by scanning. Therefore, a sequence of fingerprint images can be picked up in a predetermined time.

The image data picked up by the fingerprint sensor 1 is transformed into binarized data in the circuit 2 for digitizing (i.e., binarizing) the fingerprint data. The binarization is carried out such that, for example, "1" indicates a ridge line, and "0" indicates a groove line of a fingerprint. The output of the circuit 2 is supplied to the binarized data storing circuit 3. In the binarized data storing circuit 3, each of the sequence of the frame memories stores one fingerprint image. That is, a first fingerprint image data $D_1$ is stored in the first frame memory, a second $D_2$ the second frame memory, and so on, and an n-th $D_n$ in the n-th frame memory.

In the registration mode, the sequence of data $D_1$, $D_2$, ... $D_n$ is read from the binarized data storing circuit 3 and the read sequence is supplied to the line thinning processing circuit 4. In the line thinning processing circuit 4, a line thinning of ridge lines and groove lines of the fingerprint image data of the data sequence $D_1$, $D_2$, ... $D_n$ is carried out to attain information compression.

The output of the line thinning processing circuit 4 is supplied to the minutia extraction circuit 5. In the minutia extraction circuit 5, an extraction of minutia of the fingerprint image data, such as an end point and a branching point, on the basis of the line information from the line thinning processing circuit 4 is carried out, and the extracted minutia data, such as data of the coordinates of the position of the extracted minutia, is supplied to the data file device 6 and the comparison circuit 7.

Figures 4, 7:
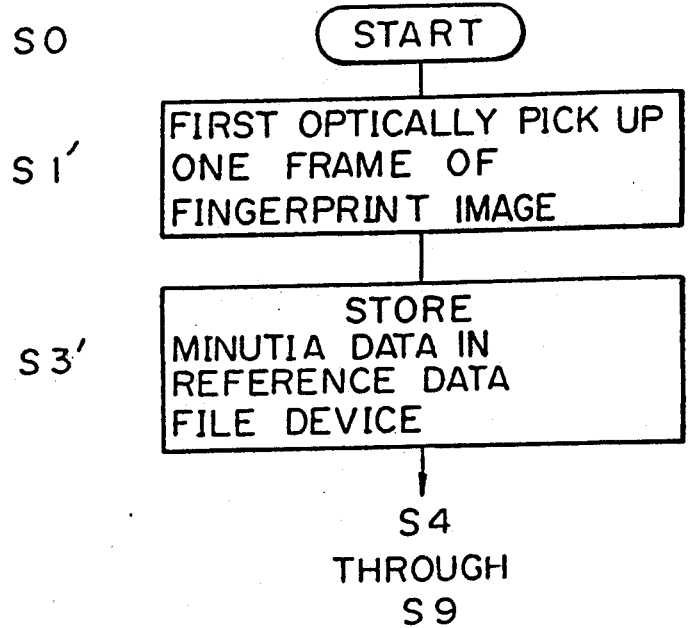
Figure 5A:
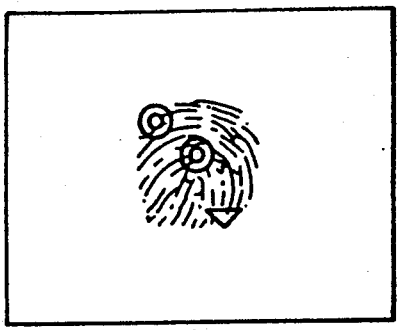
FIGS. 5A to 5D show an example of a sequence of fingerprint images over an elapse of time.
Figure 5B:
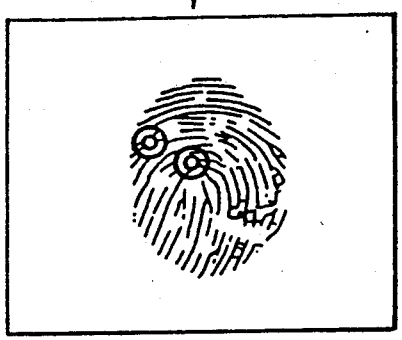
Figure 5C:
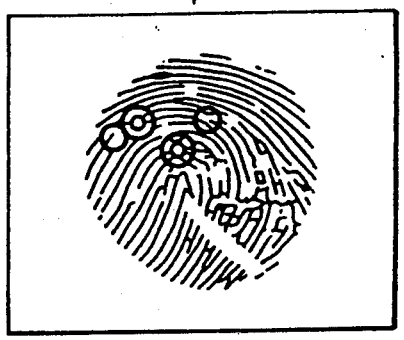
Figure 5D:

The data file device 6 receives the minutia data from the minutia extraction circuit 5 and the frequency of appearance data from the comparison circuit 7, and stores the received minutia data and the appearance frequency data in the file form. This file form is illustrated in FIG. 4. The appearance frequencies $W_1$, $W_2$, ... $W_m$ are stored in the right column and the corresponding coordinates of the positions of the extracted minutia, $(X_1, Y_1)$, $(X_2, Y_2)$, ... $(X_m, Y_m)$ are stored in the left column. In the comparison circuit 7, the minutia data from the minutia extraction circuit 5 is compared with the coordinate data stored in the data file device 6, to determine whether or not the former data coincides with the latter data. When the compared data coincide, an appearance frequency signal is supplied from the comparison circuit 7 to the data file device 6 and the appearance frequency for the corresponding minutia stored in the data file 6 is, for example, incremented by one. Thus, in the line thinning processing circuit 4, the minutia extraction circuit 5, and the comparison circuit 7, the line thinning process, the minutia extraction process, and the comparison process are executed for all of the fingerprint image data stored in the frame memories in the binary value data storing circuit 3, and based on this execution, all of frequency designated minutia data are stored in the data file device 6.

In the registered data selection circuit 8, a plurality of minutia data in the order from the highest appearance frequency to the lowest, is selected from the minutia data stored in the data file device 6. An instruction signal for extracting a portion of the fingerprint image having its center at the coordinates of the above-mentioned selected minutia from the registered data selection circuit 8, is supplied to the binarized data storing circuit 3. The binarized data from the binarized data storing circuit 3 extracted by the extraction instruction signal from the registered data selection circuit 8 is stored in the dictionary circuit 9. Thus, in the dictionary circuit 9, partial binarized data, as registered data, having their centers at the plurality of minutia selected by the registered data selection circuit 8, are stored.

The operation of the apparatus of FIG. 3 in the registration mode is now described. First, a fingerpad of a person in question is pressed onto the inspection plate of the fingerprint sensor 1 and the fingerprint image of this fingerpad is picked up by the fingerprint sensor 1. The period of the single operation of the fingerpad in the single direction onto the inspection plate is, for example, one second. Since the pressing of the fingerpad is required to be carried out carefully so as not to deviate from the fingerprint pressing state, the motion from coming into soft contact of the fingerpad with the inspection plate to a tight contact of the entirely of the fingerprint with the inspection plate is carried out slowly and takes a considerable time, such as about one second. If the speed of the picking-up operations of the fingerprint image by the fingerprint sensor 1 is 30 frames per second, 30 groups of fingerprint image data, i.e., 30 frames, are picked up during a pressing of the fingerpad for one second.

From the picked-up 30 frames, a number of frames of low reliability, which were picked-up in the beginning of the period of the pressing of the fingerpad, are rejected, and the remaining number of frames are stored in the frame memories in the binarized data storing circuit 3.

The fingerprint image data stored in the frame memories in the binarized value data storing circuit 3 are read successively, and the successively read data are processed in the line thinning processing circuit 4, processed in the minutia extraction circuit 5, and again processed in the comparison circuit 7. After these processes, the minutia coordinate data and the appearance frequency thereof are stored in the data file device 6 in the form as illustrated in FIG. 4.

Based on the sequence of the minutia coordinates in the order from the highest appearance frequency toward the lower in the data file device 6, binarized data in the binarized storing circuit 3 is extracted, and the extracted partial binarized data is stored as the registration data in the dictionary circuit 9.

A sequence of fingerprint images which are picked up during the pressing of the fingerpad onto the inspection plate over the elapse of time: i.e., time-1, time-2, time-3, and time-4, is illustrated in FIG. 5. In FIG. 5, the double circle "◉" denotes the minutia which appears with the highest frequency through time-1, time-2, time-3, and time-4. The single circle "o" denotes the minutia which appears with the next highest frequency. The inverted triangle "▽" denotes the minutia which appear with still the next highest frequency. Thus, the frequency of appearance is the highest for the minutia of the double circle "◉", intermediate for the minutia of the single circle "o", and the lowest for the minutia of the inverted triangle "▽".

In the apparatus of FIG. 3, mainly the minutia point of the double circle "◉" is used for the registration data.

The operation of the apparatus of FIG. 3 in the comparison mode will be described next. The fingerprint image data of 30 frames picked up by the fingerprint sensor 1 are supplied to the binarization circuit 2 where the image data is transformed into binarized data. The output of the circuit 2 is supplied to the binarized data storing circuit 3. In the binarized data storing circuit 53, each of the sequence of the frame memories stores one fingerprint image.

In the comparison operation, the binarized data stored in a single specific frame memory of the binarized data storing circuit 3 is compared with the data registered in the dictionary circuit 9. In accordance with the result of the comparison, a coincidence signal or a non-coincidence signal is delivered. This single specific frame memory is selected from frame memories in which a plurality of minutia image data are stored, in accordance with predetermined criteria.

Through experience, it has been acknowledged that such a single specific frame memory is often derived from the frame memories corresponding to the latter half of the period of the pressing of the fingerpad onto the inspection plate.

The operation of an apparatus for fingerprint identification according to another embodiment of the present invention is illustrated in FIG. 6.

The registration process in which the reference data is registered in the reference data file device is represented by steps S1, S2, and S3. In the registration process, a fingerpad of the person to be registered is pressed on the plate of the fingerprint sensor. The pressure of the fingerpad is increased from an initial low value gradually to higher values to reach a predetermined constant high value. During this increase of the pressure, the fingerprint image is optically picked up every 1/30 second; the optically picked up fingerprint image is analog-to-digitally converted into digital data; the converted digital data is supplied to the binarization circuit where the binarization of the converted digital data is carried out; the binarized data is stored into the first frame memory; the next fingerprint image is optically picked up; and the obtained data is stored into the second frame memory, and so on.

In the above-described process, the fingerpad is not constantly in contact with the plate of the fingerprint sensor, in that the state of the contact of the fingerpad with the plate of the fingerprint sensor changes with time in such a manner that sweat from the fingerpad may occur and the pressure of the fingerpad is varied. Therefore, although the locations of the appearance of the fingerprint pattern (i.e., image) data are almost always the same, different fingerprint pattern data can be stored in the frame memories.

In the minutia data extraction and comparison circuit, the binarized data are read in succession from the sequence of the frame memories, and the checks concerning at which location the minutia data exist are carried out. The results of the checks are stored in a storage for minutia data.

In the minutia data extraction and comparison circuit, the search for the content of the storage for minutia data is carried out thereby to count the number of the same minutia data existing at the same location. The results of the counting are arranged according to the order from the highest to the lowest. A predetermined number of the minutia data from the highest result of the counting is stored in the reference data file device.

The comparison process in which the comparison of the second picked up fingerprint image data in question with the reference minutia data read from the reference data file device is represented by steps S4, S5, S6, S7, S8, and S9. In the comparison process, the process of optical picking up of the fingerprint image and storing of the picked up fingerprint image data in the binarized data form into the frame memories is the same as in the registration process.

Next, the minutia data read from the frame memories are successively compared with the minutia data read from the reference data file device. The results of the comparison are stored in a storage.

In this comparison process, when the number of minutia data read from the storage which coincide with the minutia data read from the reference data file device is more than a predetermined threshold value, it is determined that the fingerprint is identified as coincident.

Instead of the above-described process illustrated in the flow chart of FIG. 6, it is possible to extract the minutia data from only one frame of fingerprint image data to be registered in the reference data file device, and to compare the minutia data read from a plurality of frame characteristic point data with the minutia data read from the reference data file device as illustrated in the flow chart of FIG. 7.

Figure 8:
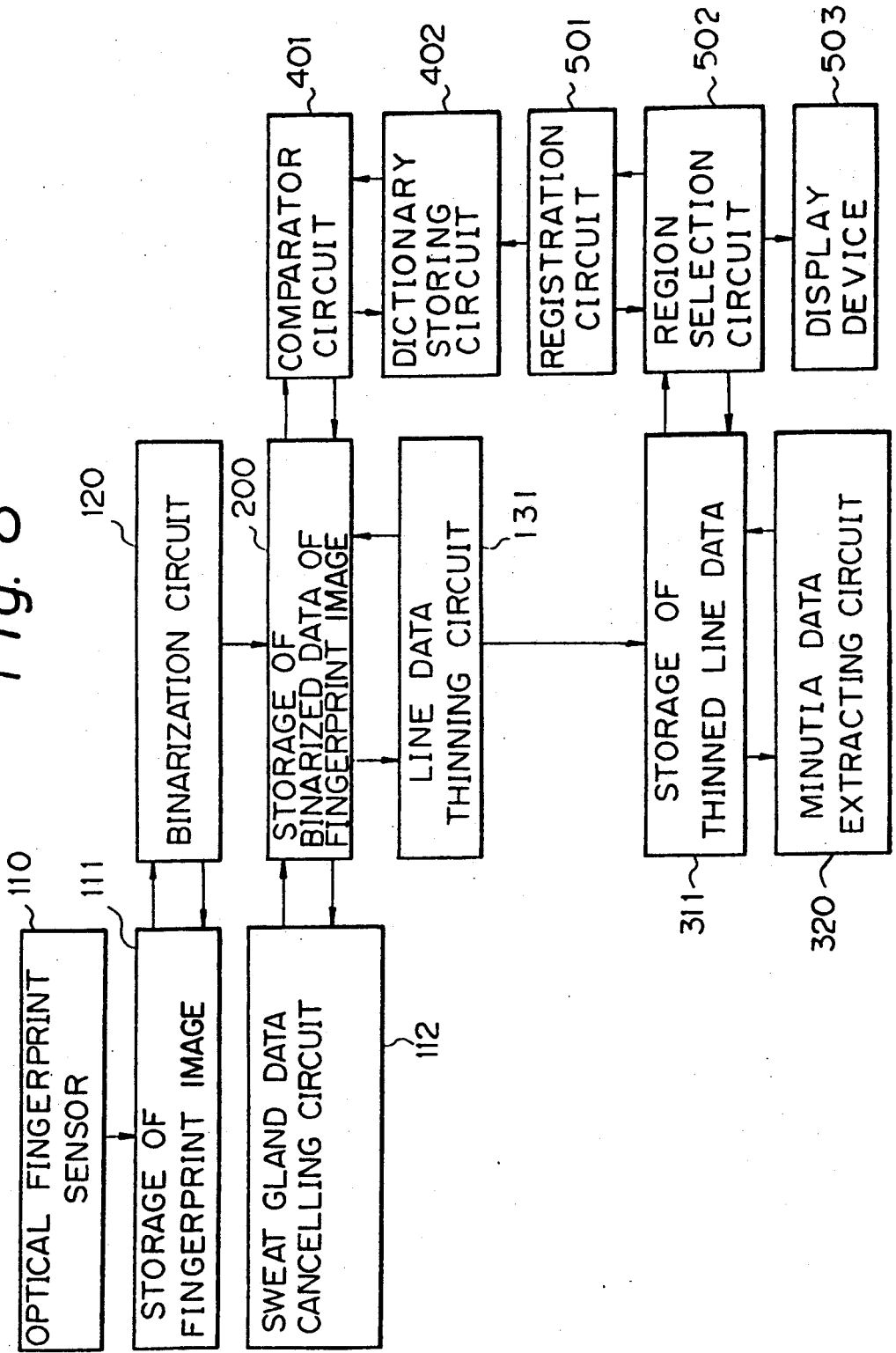
FIG. 8 is a schematic diagram of an apparatus for fingerprint identification according to a further embodiment of the present invention.

An apparatus for fingerprint identification according to a further embodiment of the present invention is illustrated in FIG. 8. The process of operation of the apparatus of FIG. 8 is illustrated in the flow chart of FIG. 9. The apparatus of FIG. 8 is constituted by an optical fingerprint sensor 110, a storage for fingerprint images 111, a binarization circuit 120, a sweat gland data cancelling circuit 112, a storage of binarization data of fingerprint image 200, a fine line thinning circuit 131, a storage of thinned line data 311, a characteristic point data extracting circuit 320, a comparator circuit 401, a dictionary storage circuit 402, a registration circuit 501, a region selection circuit 502, and a display device 503.

Figure 10:
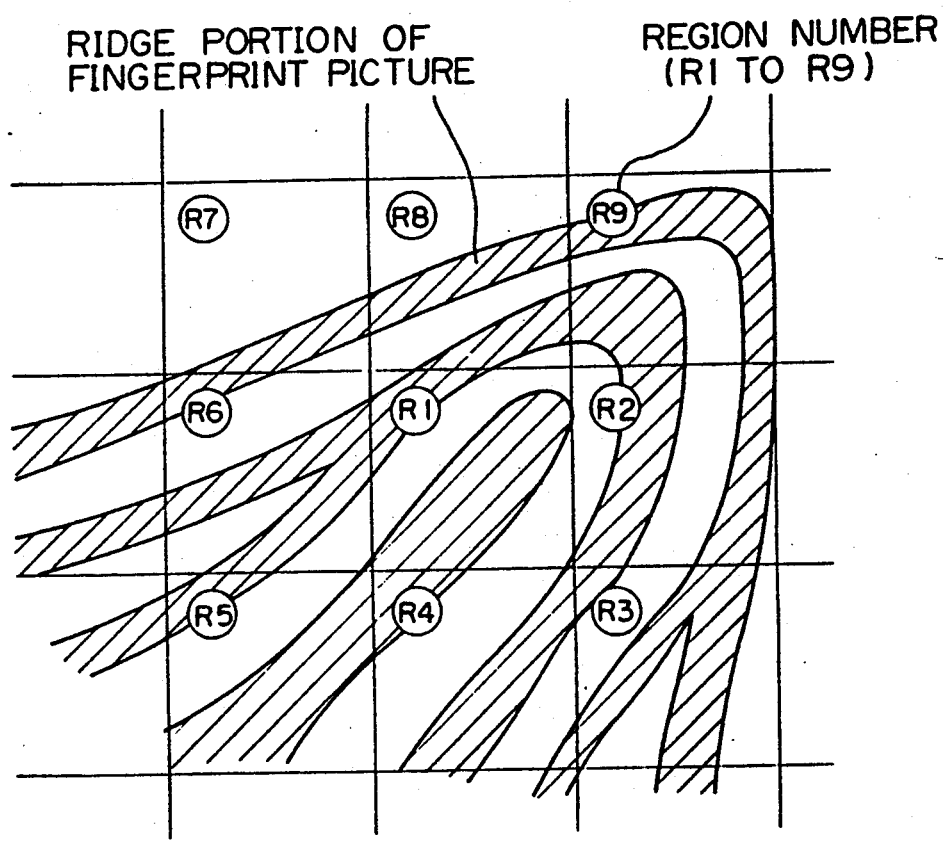
FIG. 10 shows the fingerprint image in relation with the operation of the apparatus of FIG. 8.

The operation of the apparatus of FIG. 8 is described with reference to FIG. 10 showing a fingerprint image, in which the ridge lines are represented by the hatched portions and the groove lines are represented by blank portions, and the arrangement of regions R1 to R9.

In the region selection circuit 502, the central square region R1 is set as the region accommodating a distinguished point as a minutia and a plurality of square regions R2 to R9 are set as the regions adjacent to the central square region R1, in accordance with the central region designation information. Usually many specific patterns of the fingerprint exist in these regions R1 to R9.

The binary value fingerprint image data concerning the regions R1 to R9 are supplied to the registration circuit 501.

Figure 11:
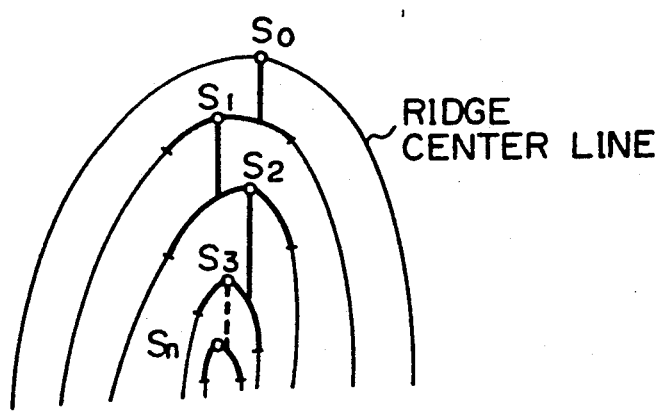
FIG. 11 shows a prior art method for obtaining the central region designation information for explaining the operation of the apparatus of FIG. 8.

The central region designation information can be obtained in accordance with known methods such as shown in FIG. 11 disclosed in Japanese Unexamined Patent Publication (Kokai) No. 60-84677. In FIG. 11, the curves are ridge center lines, $S_0$ is a start point, $S_1$, $S_2$ . . . are a sequence of vertex points, and $S_n$ is the ultimate point.

In the registration circuit 501, the data of the regions R1 to R9 are extracted and the extracted data are registered into the dictionary storing circuit 402. In the comparator circuit 401, a comparison between the binarized data from the storage of binarized data of fingerprint image 200 and the data read from the dictionary storing circuit 402 is carried out, and the result of the comparison is indicated by an indication device such as an indicator lamp (not shown).

Figure 9:
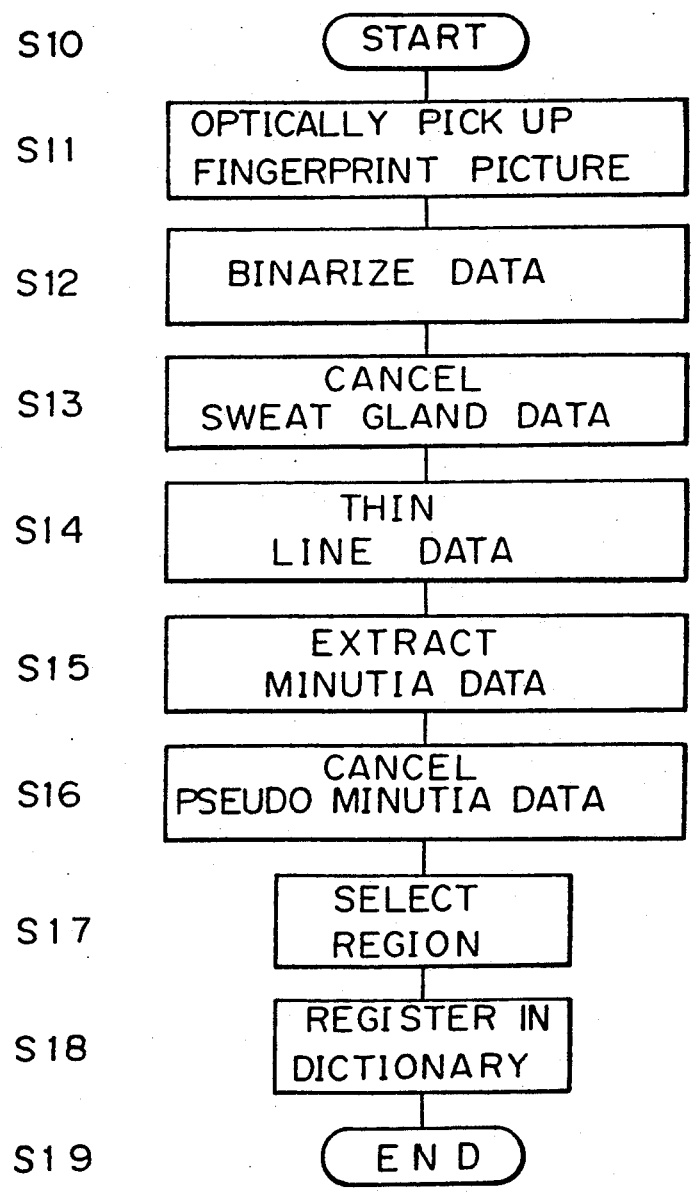
FIG. 9 shows the flow chart of the process of operation of the apparatus of FIG. 8.

The process of operation of the apparatus of FIG. 8 is explained with reference to the flow chart illustrated in FIG. 9. The process of the registration of the fingerprint image is illustrated in the flow chart of FIG. 9.

First, the fingerprint image of a person to be registered is optically picked up (S11). For example, a picture of the size of 256×256 pixels is used, and then the binarization is carried out (S12). The picture may be divided into regions, each constituted by 16×16 pixels, the average color density of each region may be calculated to provide a threshold color density value, and the binarization may be carried out by using this threshold color density value.

The data of sweat gland in a fingerprint is cancelled to enhance the reliability of the obtained data (S13); the thinning of the line data is carried out (S14); and the extraction of the minutia is carried out (S15). In this extraction, an interruption of a fine line is recognized as a minutia of an "end point", and a branching point of a line is recognized as a "branch point" and the extractions are carried out accordingly. The cancellation of the pseudo minutia data is then carried out (S16).

The detection of the location of the distinguished point as a minutia and the setting of the central region and the plurality of adjacent regions in accordance with the detected location of the distinguished point are carried out (S17), and the registration of the set central region and adjacent regions is carried out (S18). The registration of the minutia data extracted in the step S15 and the data of the regions including the adjacent regions also may be carried out.

Instead of the setting of the central region and the adjacent regions for the binarized data, it is possible to carry out this setting for color density expressed picture data or thinned line data.

Also, instead of the nine regions R1 to R9 shown in FIG. 10, it is possible to set more than nine regions as the central region and the adjacent regions.

We claim:

1. An apparatus used in a fingerprint identification for extracting minutia data from fingerprint image data optically sensed from a fingerpad and registering data for fingerprint identification based on the extracted minutia data, said apparatus comprising:

optical sensor means, including an inspection plate having a surface, for optically producing a sequence of fingerprint image data frames during a single operation of pressing a fingerpad in a substantially transverse direction onto the surface of the inspection plate and with progressively increasing pressure over a time interval, the single operation creating an initial, soft contact of a first portion of the fingerprint on a first portion of the inspection plate surface and progressively more firm contact fingerprint on a progessively increasing portion of the of a progressively increasing portion of the inspection plate surface and the optical sensor means producing the sequence of the fingerprint image data frames at spaced time increments over the time interval;

processing means for identifying and extracting minutia data and respectively associated minutia coordinate data from each of the sequence of fingerprint image data frames and for selecting, therefrom, minutia data for storage in accordance with the order of the respective frequencies of appearance of the minutia data, for the respectively corresponding minutia data coordinates thereof, as identified and extracted from the sequence of fingerprint image data frames; and data storing means for storing the selected fingerprint minutia data, as extracted from the fingerprint image data of the sequence of fingerprint image data frames produced during the single operation of pressing the fingerpad onto the inspection plate, the stored fingerprint image minutia data being utilizable for identification of the fingerprint.

2. A method used in a fingerprint identification for extracting minutia data from fingerprint image data optically sensed from a fingerpad and registering data for fingerprint identification based on the extracted minutia data, said method comprising the steps of:

optically producing a sequence of fingerprint image data frames during a single operation of pressing a fingerpad in a substantially transverse direction onto the surface of an inspection plate and with progressively increasing pressure over a time interval, the single operation creating an initial, soft contact of a first portion of the fingerprint on a first portion of the inspection plate surface and progressively more firm contact of a progressively increasing portion of the fingerprint on a progressively increasing portion of the inspection plate surface and the sequence of the fingerprint image data frames being produced at spaced time increments over the time interval;

identifying and extracting minutia data and respectively associated minutia coordinate data from each of the sequence of fingerprint image data frames and selecting, therefrom, minutia data for storage in accordance with the order of the respective frequencies of appearance of the minutia data, for the respectively corresponding minutia data coordinates thereof, as identified and extracted from the sequence of fingerprint image data frames; and storing, in a storage device, the selected fingerprint minutia data extracted from the fingerprint image data of the sequence of fingerprint image data then produced during the single operation of pressing the fingerpad onto the inspection plate, the stored fingerprint image minutia data being utilizable for identification of the fingerprint.

3. A method for identifying a fingerprint based on extractions of minutia data from fingerprint image data optically sensed from a fingerpad, said method comprising the steps of:

optically obtaining a sequence of frames of fingerprint image data for registration during a single operation of pressing a fingerpad onto an inspection plate in a direction substantially transverse to the plate and with progressively increasing pressure, over a time interval;

storing the obtained fingerprint image data for registration in a storage device in the form of a sequence of frames of fingerprint image data for registration;

extracting minutia data for registration, from the stored sequence of frames of fingerprint image data for registration;

storing the extracted minutia data for registration into a reference data file device in accordance with the order from the most frequently appearing minutia, in succession, to the least frequently appearing minutia;

optically obtaining a sequence of frames of fingerprint image data for comparison during a single operation of pressing the fingerpad in single direction onto the inspection plate;

storing the obtained fingerprint image data for comparison in the storage device in the form of a sequence of frames of fingerprint image data for comparison;

extracting minutia data for comparison from the stored sequence of frames of fingerprint image data for comparison;

comparing the minutia data for comparison, extracted from the stored sequence of frames of fingerprint image data for comparison, with the minutia data for registration, as stored in said reference data file device for determining points of coincidence therebetween; and determining a coincidence between fingerprints, as respectively represented by the minutia data for comparison and the minutia data for registration, when the number of points of coincidence determined in accordance with said comparing step, and in relation to one frame of the fingerprint image data, is greater than a predetermined number.

4. A method according to claim 3, further comprising the steps of:

extracting a plurality of regional fingerprint image data from regions surrounding the region of the most frequently appearing minutia, in addition to the extraction of the most frequently appearing minutia; and storing the extracted plurality of regional fingerprint picture image data in the reference data file device, in addition to the storing of the most frequently appearing minutia.

* * * * *

UNITED STATES PATENT AND TRADEMARK OFFICE
CERTIFICATE OF CORRECTION

PATENT NO. : 5,109,428
DATED : April 28, 1992
INVENTOR(S) : Seigo Igaki, et. al.

It is certified that error appears in the above-indentified patent and that said Letters Patent is hereby corrected as shown below:

Title PAGE: Please insert the following:

item     --[73] Assignee: Fujitsu Limited, Kawasaki, Japan--.

Col. 2,  line 16, change "utilize a" to --utilizable for--;
         line 52, change "711" to --71--.

Col. 3,  line 65, change "thnnning" to --thinning--.

Col. 4,  line 65, change "entirely" to --entirety--.

Col. 5,  line 49, change "53" to --3--.

Col. 8,  lines 33-34, delete "fingerprint on a progessively increasing portion of the";
         line 35, before "inspection" insert --fingerprint on a progressively increasing portion of the--.

Signed and Sealed this

Seventeenth Day of May, 1994

Attest:

BRUCE LEHMAN

*Attesting Officer*     *Commissioner of Patents and Trademarks*